US011481936B2

(12) United States Patent
Gemmel et al.

(10) Patent No.: US 11,481,936 B2
(45) Date of Patent: Oct. 25, 2022

(54) ESTABLISHING A THREE-DIMENSIONAL TOMOSYNTHESIS DATA RECORD

(71) Applicant: Siemens Healthcare GmbH, Erlangen (DE)

(72) Inventors: Alexander Gemmel, Erlangen (DE); Gerhard Kleinszig, Forchheim (DE); Björn Kreher, Bräuningshof (DE); Holger Kunze, Bubenreuth (DE); Jessica Magaraggia, Erlangen (DE); Markus Weiten, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 145 days.

(21) Appl. No.: 16/839,364

(22) Filed: Apr. 3, 2020

(65) Prior Publication Data

US 2020/0320755 A1 Oct. 8, 2020

(30) Foreign Application Priority Data

Apr. 3, 2019 (DE) .......................... 102019204765.3

(51) Int. Cl.
*G06T 11/00* (2006.01)
*G06T 7/00* (2017.01)

(52) U.S. Cl.
CPC .......... *G06T 11/008* (2013.01); *G06T 7/0014* (2013.01); *G06T 2207/10116* (2013.01);
(Continued)

(58) Field of Classification Search
None
See application file for complete search history.

(56) References Cited

U.S. PATENT DOCUMENTS 5,905,809 A    5/1999    Timmer
6,081,577 A *   6/2000    Webber ................ G01N 23/046
                                                                                                           378/23

(Continued)

FOREIGN PATENT DOCUMENTS

CN       1575762 A      2/2005
CN     103797517 A      5/2014
(Continued)

OTHER PUBLICATIONS

Acciavatti, Raymond J., and Andrew DA Maidment. "Oblique reconstructions in tomosynthesis. I. Linear systems theory." Medical physics 40.11 (2013): 111911. pp. 1-22.
(Continued)

*Primary Examiner* — Jiangeng Sun
(74) *Attorney, Agent, or Firm* — Lempia Summerfield Katz LLC (57) ABSTRACT

A method for establishing a three-dimensional tomosynthesis data record of a target volume from two-dimensional projection images recorded with a recording arrangement including an X-ray source and an X-ray detector in different recording geometries is provided. During or after a reconstruction step, a deconvolution technique is used for reducing image artifacts of the tomosynthesis data record occurring due to lacking information. The projection images are recorded along a linear recording trajectory of the X-ray source. The reconstruction and the use of the deconvolution technique take place in a plurality of different two-dimensional reconstruction planes that are spanned by the recording trajectory and, in each case, a definition point in the target volume.

17 Claims, 4 Drawing Sheets

(52) U.S. Cl.
CPC ............... *G06T 2207/20192* (2013.01); *G06T 2211/421* (2013.01)

(56) References Cited

U.S. PATENT DOCUMENTS

| | | | |
|---|---|---|---|
| 6,442,288 B1 | 8/2002 | Haerer | |
| 2003/0072417 A1* | 4/2003 | Kaufhold | A61B 6/583 378/207 |
| 2004/0264636 A1 | 12/2004 | Claus et al. | |
| 2005/0078862 A1 | 4/2005 | Guillemaud et al. | |
| 2007/0036418 A1* | 2/2007 | Pan | A61B 6/027 382/131 |
| 2009/0175562 A1* | 7/2009 | Pan | A61B 6/027 382/312 |
| 2011/0013817 A1* | 1/2011 | Medow | G06T 11/006 382/131 |
| 2012/0257714 A1* | 10/2012 | Graumann | A61B 6/5241 378/19 |
| 2014/0348407 A1 | 11/2014 | Nielsen et al. | |
| 2015/0238159 A1* | 8/2015 | Al Assad | A61B 6/025 378/5 |
| 2016/0071293 A1 | 3/2016 | Homann et al. | |
| 2018/0018796 A1* | 1/2018 | Chen | A61B 6/504 |
| 2018/0330233 A1* | 11/2018 | Rui | G06N 3/0454 |
| 2019/0251713 A1* | 8/2019 | Chen | A61B 6/482 |
| 2020/0054297 A1* | 2/2020 | Martinez Ferreira | A61B 6/4458 |
| 2020/0305806 A1* | 10/2020 | Tang | G06N 3/084 |
| 2020/0320755 A1* | 10/2020 | Gemmel | A61B 6/025 |

FOREIGN PATENT DOCUMENTS

| | | |
|---|---|---|
| CN | 105229702 A | 1/2016 |
| DE | 19842944 B4 | 8/2006 |

OTHER PUBLICATIONS

Jannetta, Adrian. Advanced deconvolution techniques and medical radiography. Diss. Northumbria University, 2005. pp. 1-233.

Levakhina, Yulia. Three-Dimensional Digital Tomosynthesis: Iterative reconstruction, artifact reduction and alternative acquisition geometry. Springer, 2014. pp. 1-209.

Syben, Christopher, et al. "Deriving neural network architectures using precision learning: parallel-to-fan beam conversion." German Conference on Pattern Recognition. Springer, Cham, 2018. pp. 1-15.

Syben, Christopher, et al. "Precision learning: reconstruction filter kernel discretization." arXiv preprint arXiv:1710.06287 (2017). pp. 1-4.

* cited by examiner

ESTABLISHING A THREE-DIMENSIONAL TOMOSYNTHESIS DATA RECORD

This application claims the benefit of German Patent Application No. DE 10 2019 204 765.3, filed Apr. 3, 2019, which is hereby incorporated by reference in its entirety.

BACKGROUND

The present embodiments relate to establishing a three-dimensional tomosynthesis data record of a target volume from two-dimensional projection images recorded with a recording arrangement in different recording geometries.

The reconstruction of higher dimensional image data records from lower dimensional projection images in X-ray imaging is already well known in the prior art. Thereby, usually, in different versions of computed tomography, two-dimensional projection images are recorded with a recording arrangement of an X-ray apparatus (e.g., a computed tomography apparatus), such that a reconstruction that is as complete, artifact-free, and has as high a quality as possible results. Herein, it may be provided, for example, that the X-ray source moves in a circular path about the target volume. For the complete reconstruction of the target volume, projection images may be recorded over a projection angular range of 180° plus the cone angle or fan beam angle. Thereby, other recording trajectories of the X-ray source may be provided, for example, with spiral computed tomography. The use of computed tomography approaches has also been proposed for X-ray apparatuses with a C-arm, where, for example, the C-arm may rotate about the target volume (e.g., in a patient) in order to obtain projection images from different projection directions, and therefore using different recording geometries.

Three-dimensional recordings are also often desired in the context of surgical interventions and/or in relatively complex investigations requiring many items of equipment in a confined space. For example, however, in the context of a medical intervention on a patient, there often exist temporal and spatial limitations or restrictions with regard to the radiation dose to be administered to the patient. This may have the result, for example, that a recording of a three-dimensional computed tomography data record in which, for example, a C-arm is rotated around a patient is not conceivable for temporal, spatial or radiological reasons. In contrast thereto, two-dimensional projection images do not provide all the details with sufficient visibility since structures are overlaid.

It has therefore been proposed that whenever such temporal, spatial, and/or radiological limitations exist, a tomosynthesis may be performed. Tomosynthesis is distinguished in that at least one condition of full reconstruction is significantly infringed. This provides that the recorded projection data of the projection images does not have all the information that is required for a correct reconstruction, so that approximations or the like are used. For example, a tomosynthesis with a C-arm may be carried out such that the C-arm is moved only through a small projection angle interval made up of significantly less than 180° plus cone angle or fan beam angle (e.g., 30°). This is usable significantly more temporally, spatially, and radiologically efficiently.

As previously mentioned, however, tomosynthesis reconstructions have the disadvantage that particular projection data that would permit a more exact reconstruction is not measured. This is usually expressed as a blurring of the object structures in the target volume in the direction of the central beam direction used. These blurrings and therefore the resultant artifacts may make an assessment of the resultant reconstructed three-dimensional tomosynthesis data record more difficult.

The reconstruction in a reconstruction step may be carried out according to the prior art, for example, as a filtered back projection (FBP). Hereby, the convolution kernels are determined dependent upon the projection geometry and the recording trajectory; see, in this regard, for example, DE 198 42 944 A1 or the article by R. J. Acciavatti and A. D. A. Maidment, "Oblique Reconstructions in Tomosynthesis. I. Linear Systems Theory," in: Medical Physics 40 (2013), page 111911, accessible under http://doi.org/10.1118/1.4819941.

Regarding the problem of the incompleteness of projection data in tomosynthesis that results in artifacts (e.g., blurring) in the reconstructed tomosynthesis image data record, a variety of approaches have already been proposed. One of these approaches is the use of a deconvolution technique, with the aid of which, as a postprocessing step, a deconvolution may be carried out; see, for example, Adrian Leslie Jannetta, "Advanced Deconvolution Techniques and Medical Radiography," doctoral thesis, October 2005, University of Northumbria at Newcastle. This starts from an image formation model of an imaging system in which ultimately the imaging may be carried out with a point spread function and a noise term.

The image arises through a convolution with the point spread function so that it may be assumed that by the imaging, errors arising and therefore artifacts may be at least reduced by a corresponding deconvolution. Hereby, the selection of the deconvolution kernel is of essential importance for success.

Alternative approaches for rectifying the artifacts arising due to incompleteness use iterative reconstruction methods that bring improved results with the aid of regularization; see, in this regard, for example, Yulia Levakhina, "Three-Dimensional Digital Tomosynthesis," doctoral thesis, 2013, University of Lübeck.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an improved route, as compared with the prior art, permitting, for example, the employment of artificial intelligence reduces artifacts arising as a result of incompleteness of the projection data record in tomosynthesis image data records.

The present embodiments therefore provide that the projection images are recorded along a linear recording trajectory of the X-ray source, where the reconstruction and the use of the deconvolution technique take place in a plurality of different two-dimensional reconstruction planes that are spanned by the recording trajectory and, in each case, a definition point in the target volume.

The present embodiments therefore relate to tomosynthesis in which the recorded projection data record in the form of the projection images is not complete, so that a plurality of completeness criteria necessary for a complete reconstruction are not fulfilled. In other words, the incompleteness of the projection data record infringes at least one (e.g., a plurality of) tomographic sufficiency criteria and therefore results in artifacts in the reconstructed three-dimensional tomosynthesis data record. The tomosynthesis therefore represents a volumetric imaging method that provides spatial information regarding structures in the target volume, although it is not possible to reconstruct all the spatial information. For this reason, the improvement in the image quality represents a significant field of research.

In the context of the present embodiments, for the improvement of the image quality, a deconvolution technique is used. The aim of this is, for example, to reduce the blurring arising due to the incompleteness. It is thereby attempted to substantially reverse the convolution using the point spread function. In the context of the present embodiments, for example, the usual conical beam geometry is used, which provides that, starting from the X-ray source, a beam cone that broadens toward the X-ray detector and irradiates the X-ray detector is generated.

According to the present embodiments, the projection images are recorded such that the X-ray source moves on a linear recording trajectory (e.g., mathematically, on a straight line). If all the recording points of the recording trajectory of the X-ray source lie on a straight line, then together with a point to be reconstructed in the target volume that does not lie on the recording trajectory, the recording points span a reconstruction plane. All the rays that originate from the recording points that represent X-ray source points and intersect the definition point A in the target volume necessarily lie in this reconstruction plane (e.g., two-dimensional reconstruction plane). This also applies for each further point that lies on this reconstruction plane. It may be shown that no conceivable point exists that does not lie on the reconstruction plane through which a ray of the X-ray source passes that simultaneously intersects the reconstruction plane.

This has the consequence that for the reduction of the artifacts occurring due to the incompleteness, in a point to be reconstructed, only points from the corresponding reconstruction plane are to be used. At the same time, it is the case, however, that a deconvolution rule for a reconstruction plane of this type may be used in the same way on a further reconstruction plane that lies, using another definition point, outside the initially discussed reconstruction plane, which is rotated, for example, by an angle about the recording trajectory. Formulated differently, by the use of a straight line as the recording trajectory, a type of "book" arises, with the two dimensional pages being the reconstruction planes. It is otherwise advantageously the case with the deconvolution kernel, which may be selected to be the same for all these reconstruction planes, that proximity relationships between planes rotated relative to one another that may be used, for example, for a further reduction of artifacts, also apply equally for all these reconstruction planes, apart from the edge reconstruction planes.

Summarizing, this provides that a three-dimensional problem is converted through skillful selection of recording parameters (e.g., the course of the recording trajectory) into a two-dimensional problem on a plurality of reconstruction planes. On these reconstruction planes, the reconstruction may be carried out entirely independently, and the reconstruction planes are also independent of one another with regard to the blurring effects. The same deconvolution rule (e.g., the same deconvolution kernel) may also be used. In this way, the complexity is significantly reduced, not only in relation to the reconstruction, but also with regard to the use of the deconvolution technique, so that, for example, the use of artificial intelligence is also enabled (e.g., a neural network reduced in complexity compared with the three-dimensional case), and this will be considered in greater detail below.

For the selection of the definition points for defining the different reconstruction planes to which both the reconstruction and also the deconvolution technique are applied, different approaches may be provided. Thus, it is possible, for example, to select the definition points to be along a circular segment in the target volume around the recording trajectory. In one embodiment, the selection takes place dependent upon the desired resolution of the tomosynthesis data record. Also, at least one position of detector rows may be utilized for the definition. A wide variety of approaches may be provided for defining corresponding two-dimensional reconstruction planes that cover the target volume, completely and sufficiently densely, in order to obtain the tomosynthesis data record in the desired resolution.

If the relative geometry of the recording arrangement (e.g., of the X-ray detector in relation to the X-ray source; therefore, the projection geometry) changes during the recording of the projection images as will be described in greater detail below, the projection data of the projection images may be converted into a fixed, specified, relative geometry (e.g., projection geometry). For example, for each projection image with a deviating relative geometry (e.g., projection geometry), a virtual detector that corresponds in relative position to that of the X-ray detector in the corresponding reference geometry may be defined. In one embodiment, the detector rows of the virtual detector may each be assignable to a reconstruction plane. Corresponding conversion methods are already known from the prior art and are not described in detail here.

Since the use of tomosynthesis has also proved to be particularly suitable for medical interventions and examinations and since with such medical interventions and/or examinations, X-ray apparatuses with a C-arm are often used, in the context of the present embodiments, a recording arrangement arranged on a C-arm is used. With a C-arm, on provision of the corresponding movement degrees of freedom, a linear recording trajectory of the X-ray source may be enabled. Thus, in a first embodiment, the recording trajectory may be realized at least partially by a movement of the C-arm perpendicularly to a plane of extension.

Independently of a C-arm, a linear tomograph or the like with other configurations of recording arrangements may be realized, for example, when using X-ray apparatuses provided for the radiography of longer body portions, or the like.

The main movement intended for a C-arm is rotation about the isocenter, which is also used, for example, in order to realize a circular path as the recording trajectory of the X-ray source. The advantage of such a rotation movement is that a target volume situated in the isocenter (e.g., centrally between the X-ray source and the X-ray detector) is in principle situated in the acquisition region of the recording arrangement. According to the present embodiments, i with a C-arm, the rotation may be used, and a linear recording trajectory of the X-ray source may be realized.

For this purpose, in one embodiment, it may be provided that on a rotation of the C-arm (e.g., while maintaining the alignment of the X-ray source to a point, such as the central point, of the target volume) the recording arrangement is moved in a compensating manner along the central ray of the recording arrangement. In other words, this provides that by the compensation of the movement of the X-ray source that takes place along a circular path during the rotation, the isocenter of the C-arm and the X-ray detector move along the direction of the central ray of the recording arrangement.

Thereby, a combination of such possibilities for producing a linear recording trajectory of the X-ray source may also be provided.

In a third variant, which like the C-arm rotation approach is also directed to, in order to keep target volumes along the linear recording trajectory as far as possible in the acquisition region of the recording arrangement, it being provided that after a subsection of the movement of the X-ray source along the recording trajectory with a parallel movement of the X-ray detector, a rotation of the recording arrangement around the X-ray source takes place. The rotation of the recording arrangement around the X-ray source takes place such that the target volume is situated in the acquisition region of the recording arrangement, whereupon the movement of the X-ray tube along the recording trajectory is continued with a parallel movement of the X-ray detector. This provides that the recording arrangement may perform a rotation movement around the X-ray source in order to convert parallel movements of the X-ray source and the X-ray detector in different angular positions of the central ray in relation to the target volume. In this way, the greatest possible region coverage of long objects is enabled. For example, different individual recording geometries may be implemented here, although a linear recording trajectory is still used, and the target volume remains in the acquisition region of the recording arrangement. In other words, an optimum space utilization is realized. It is also possible to implement the rotation about the X-ray source by partial movements of the recording arrangement (e.g., on use of a C-arm).

As already mentioned, the reduction of the deconvolution problem (and also the reconstruction problem) to two dimensions opens up the possibility for the use of algorithms of artificial intelligence or machine learning that are significantly reduced in complexity and computation effort. Therefore, one development of the present embodiments provides that a deconvolution algorithm of artificial intelligence that has been trained by machine learning and is to be used for the deconvolution, which describes a deconvolution kernel or determines an item of deconvolution information that describes a deconvolution kernel and is to be utilized for the deconvolution in all the reconstruction planes, is used. This provides that either the deconvolution algorithm, while describing a particular deconvolution kernel, may carry out the deconvolution itself once the deconvolution algorithm has been suitably trained in advance, or, once the deconvolution algorithm has been suitably trained, the deconvolution algorithm may supply an item of deconvolution information (e.g., therefore parameters that describe a deconvolution kernel) and may be used in a conventional deconvolution algorithm or even a reconstruction algorithm that then contains the deconvolution. Thereby, a large number of variants are known and have already been proposed and may also be used in the context of the present embodiments, so that only some examples are to be described in detail. In one embodiment, in each case, a neural network may be used as a deconvolution algorithm (e.g., a deep neural network (DNN)) and/or a convolutional neural network (CNN)).

In one exemplary embodiment, it is possible that the reconstruction takes place on the reconstruction planes, where a known reconstruction method from the prior art may be used for the two-dimensional reconstruction on each reconstruction plane. Due to a high efficiency, in the context of the present embodiments, methods of filtered back projection may be used, for example. On these reconstruction planes (e.g., still in two dimensions), subsequently to the reconstruction, the deconvolution may take place. For this purpose, for example, a trained deconvolution algorithm (e.g., a deep neural network) may be used, where the deconvolution algorithm may obtain as input data, for example, at least one reconstructed slice image of the reconstruction plane and may output a correspondingly deconvoluted (e.g., restored) slice image.

In another embodiment, which is considered in detail in an actual example below, it the reconstruction and the deconvolution may be implemented in a single deconvolution algorithm of artificial intelligence. Herein, for example, concepts of precision learning may be used, by which any desired filter kernels (e.g., therefore also convolution kernels or deconvolution kernels) may be determined in the context of machine learning. For example, in an article by C. Syben et al., "Precision Learning: Reconstruction Filter Kernel Discretization," arXiv: 1710.06287, it is proposed to use a DNN in order to discretize the ideal continuous reconstruction filter. Thereby, it may be shown for this case, for example, that the filter learned there is not object-dependent, so that the concept described there thus enables filter kernels to be taught that may be generally used for the particular overall recording geometries used (e.g., therefore projection geometries and recording geometries). In this context and for use with other problems, reference is also made to the article by C. Syben et al., "Deriving Neural Network Architectures Using Precision Learning: Parallel-to-Fan Beam Conversion," arXiv: 1807.03057.

For the training of the deconvolution algorithm, in general, the result of a simulation and/or a scan (e.g., with a phantom) may be used as training data. Thereby, actually recorded scan data may be used as training data (e.g., for the scan with a phantom), as described, for example, in the first-mentioned article by C. Syben, although a simulation may be used instead. For this purpose, for the simulation, virtual projection images of a known object are calculated, and/or at least one noise effect is added in the context of the simulation. For example, it is thus possible to generate simulated projections of a computed tomography volume that is already recorded and is therefore known as self-evident fact, of an anatomical region of interest (e.g., corresponding to the target volume). For this purpose, therefore, two-dimensional virtual projection images are calculated and, for example, on subsequent activation of the deconvolution algorithm after the reconstruction step, are reconstructed by the selected reconstruction method. In addition, a different degree of noise may also be added. In this way, a large quantity of training data may be generated. With the aid of the training data, the deconvolution algorithm may be trained (e.g., as a DNN).

In one embodiment, on training the deconvolution algorithm, at least one additional optimization condition is used for further improvement of the image quality (e.g., a low-pass filtration and/or an edge enhancement). If, for example, during training of the deconvolution algorithm, a particular target function that is usually directed toward a best possible match with the ideally known self-evident fact is used, kernels may be enhanced, and the further image quality enhancement measures may be effectively "integrated" into the deconvolution kernel obtained from the training. Thus, for example, edges may be better enhanced, or a low-pass filtration may be used.

Thereby, in this context, such an approach with a modified target function may, for example, be applied if the aforementioned framework by C. Syben et al. is used. Then, a use of particular weights on the filtered back projection may lead to not only the deconvolution being integrated into the filtered back projection, but in addition, further particular properties being integrated into the resulting deconvolution kernel in that the cost function is modified accordingly during training of the deconvolution algorithm. In other words, when the reconstruction takes place on the reconstruction planes according to the method of the filtered back projection, the deconvolution may be carried out integrated into the reconstruction, optionally also using additional optimization conditions for further improvement of the image quality.

In one embodiment, as an additional step after the deconvolution, an adjustment making use of a proximity relationship between two adjacent reconstruction planes may be carried out. In this way, it may be provided that deconvolution results of different reconstruction planes are adjusted to one another, if necessary, so that jumps or suchlike between adjacent reconstruction planes are prevented. For example, an L1-norm optimization between adjacent reconstruction planes may be provided as an additional act. Other additional acts provided, for example, for smoothing the transitions between the reconstruction planes may also be provided. In addition, the advantage arises thereby that due to the linear recording trajectory used and the reconstruction planes thus arising that may be understood as like book pages that may be observed two-dimensionally and may be regarded as substantially equivalent, the respective proximity relationships are also or may ultimately be selected to be the same.

In one embodiment, the tomography image data record may be determined by reformatting and/or converting the information available regarding the reconstruction planes into a three-dimensional image matrix describing voxels. In this way, a "standardized" tomosynthesis data record that may easily be represented is obtained based on a suitable reformatting/conversion with conventional image viewers. For example, sectional images that lie parallel to the X-ray detector in the central projection geometry or another defined recording geometry (e.g., that of the aforementioned virtual detector) may thereby be striven for. Other definitions of an image matrix are also possible.

In addition to the method, the present embodiments also relate to an X-ray apparatus having a recording arrangement having an X-ray source and an X-ray detector, and a control device configured for carrying out the method according to one or more of the present embodiments. All descriptions regarding the method according to the present embodiments apply similarly to the X-ray apparatus according to the present embodiments, so that the aforementioned advantages may therefore also be achieved therewith.

The control device may thereby have at least one processor and at least one storage device. For the performance of the different acts of the method according to the present embodiments, the control device may also have corresponding functional units that may be implemented by hardware components and/or software components. For example, a recording unit for controlling the recording of the projection images and correspondingly also for setting the corresponding recording geometries may be used. A reconstruction unit and a deconvolution unit may be used, where the deconvolution unit may also be integrated into the reconstruction unit, as shown. Further functional units relating to further embodiments, for example, for reformatting may be provided.

A computer program according to the present embodiments is, for example, directly loadable into a memory store of a control device of an X-ray apparatus and has program means in order to carry out the acts of a method according to the present embodiments when the computer program is executed in the control device of the X-ray apparatus. The computer program may be stored on an electronically readable data carrier (e.g., a non-transitory computer-readable storage medium) according to the present embodiments. The non-transitory computer-readable storage medium therefore includes electronically readable control information (e.g., instructions) stored thereon. The electronically readable control information includes at least one computer program according to the present embodiments and is configured such that, on use of the data carrier in a control device of an X-ray apparatus, the computer program carries out a method according to the present embodiments. The electronically readable data carrier according to the present embodiments is, for example, a non-transient data carrier (e.g., a CD-ROM).

DETAILED DESCRIPTION

Figure 1:
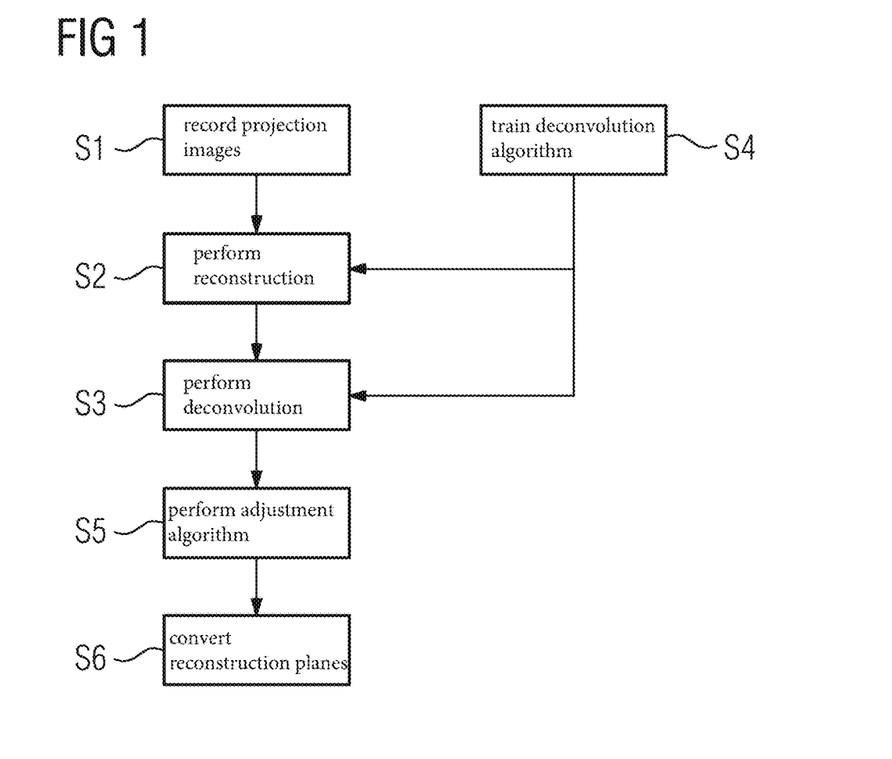
FIG. 1 is a flow diagram of an exemplary embodiment of a method.

FIG. 1 shows a flow diagram of an exemplary embodiment of a method, where, for example, during a medical intervention (e.g., a surgical procedure and/or an examination of a patient), a three-dimensional (3D) tomosynthesis data record of a target volume of a patient is to be recorded (e.g., with as little as possible essential movement of a C-arm that carries the recording arrangement including an X-ray source and an X-ray detector), a 3D reproduction of the target volume that is as high-quality as possible is to be achieved.

For this purpose, in act S1, projection images are recorded using different recording geometries; the X-ray source, however, moves along a linear recording trajectory (e.g., a straight line). This has the advantage that with the X-ray geometry used, a plurality of two-dimensional reconstruction planes may be defined in the manner of book pages, which in relation to the reconstruction and a deconvolution to be carried out for reducing the blurring due to non-recorded projection, data may be regarded independently and as a two-dimensional problem.

Figure 2:
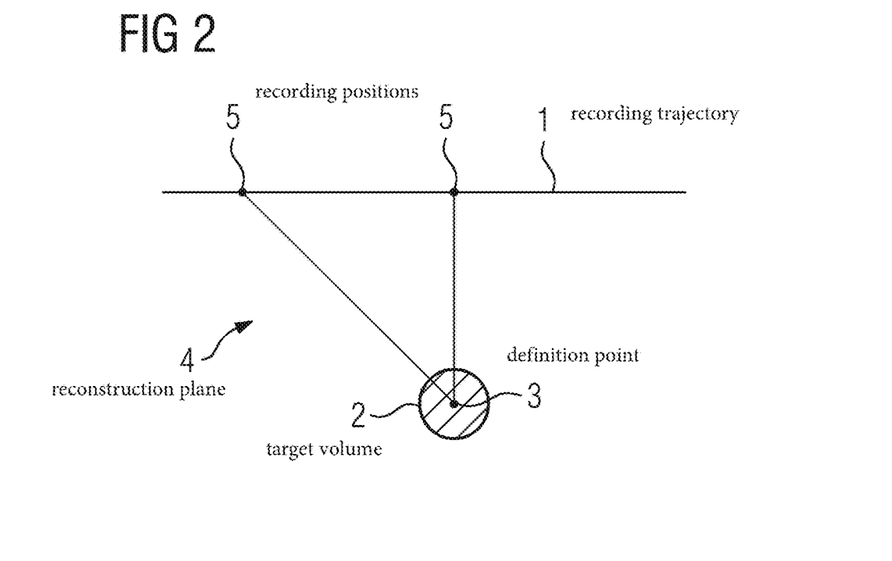
FIG. 2 is an exemplary representation for the definition of reconstruction planes.

FIG. 2 shows, by way of example, the recording trajectory 1 forming a straight line as the recording trajectory 1 extends past an indicated target volume 2. Together with a definition point 3 to be reconstructed within the target volume 2, the recording trajectory 1 spans a reconstruction plane 4 (e.g., the drawing plane), since all the X-ray rays that emanate from recording positions 5 (e.g., X-ray source points) on the recording trajectory 1 and intersect the definition point 3 lie in the reconstruction plane 4. This applies also for each further point that is to be reconstructed in the target volume 2 and that lies within the same reconstruction plane 4. It may be shown that no point to be reconstructed in the target volume 2 exists that does not lie on the reconstruction plane 4 and through which a ray of the X-ray source extends and simultaneously intersects the reconstruction plane 4.

This provides, however, that the reconstruction and deconvolution techniques for the reduction of the blurring (e.g., in the definition point 3) are to only use points from the reconstruction plane 4. A deconvolution rule for a reconstruction plane 4 may, however, equally be applied to a further reconstruction plane that, for example, is rotated by an angle through which the recording trajectory 1 intersecting the recording positions 5 is rotated. If also proximity relationships between reconstruction planes 4 rotated relative to one another are used for reducing the blurring, then these, apart from the reconstruction planes 4 positioned at the edge, are also equally usable for all the reconstruction planes 4.

For the definition of the different reconstruction planes 4, for example, definition points 3 lying on a circular segment of a circle about the recording trajectory 1 may be used. Spacing of the definition paints 3 may be selected, for example, dependent upon a resolution of the tomosynthesis data record to be achieved later. Other possibilities for the definition of the reconstruction planes 4 are usable.

Figure 3:
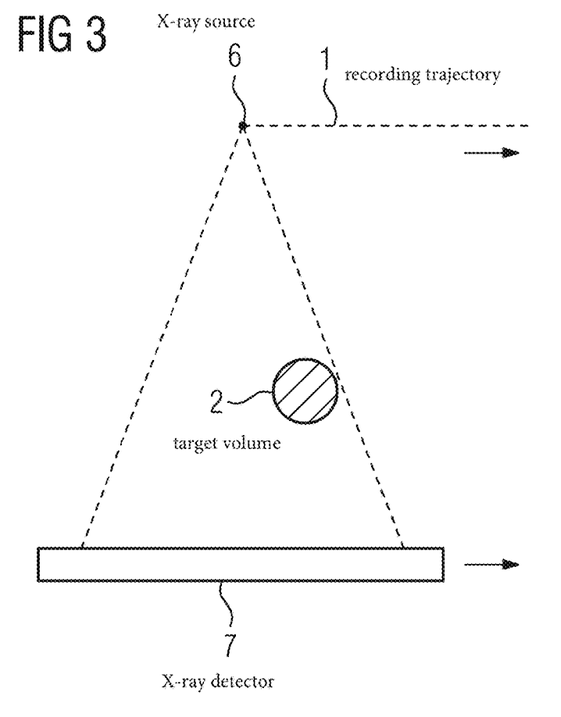
FIG. 3 illustrates a first possibility for realizing a use of a linear recording trajectory.

FIG. 3 shows a first possibility that is easily implementable but may be less preferred for realizing a linear recording trajectory 1 of this type. This, however, may also be used partially in other variants. The X-ray source 6 and the X-ray detector 7 are each moved parallel past the target volume 2 so that the X-ray source 6 moves along the recording trajectory 1. Projection images come about, making use of different recording geometries, that show the target volume 2. If something of this type is used, the number of the different recording geometries and corresponding variance is, however, more likely to be restricted. In addition, the target volume 2 is more likely to be situated in many projection images at the edge of the projection image.

Figure 4:
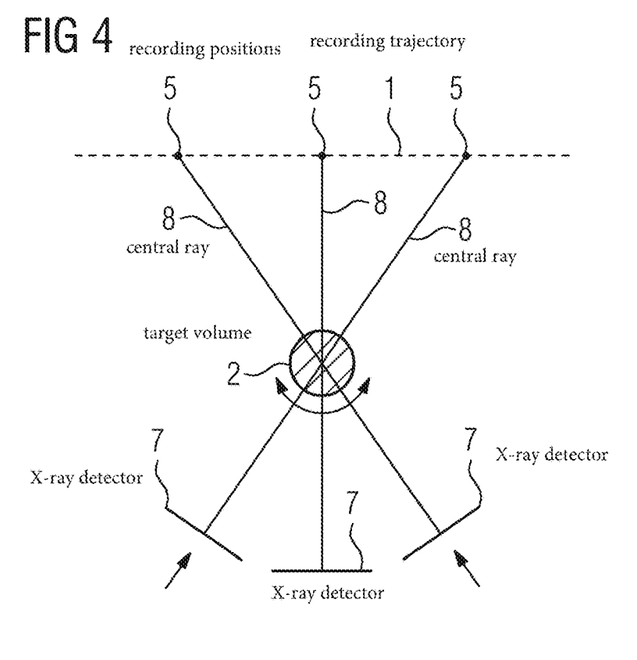
FIG. 4 illustrates a second possibility for realizing a linear recording trajectory.

FIG. 4 shows a second possibility for realizing the linear recording trajectory 1 with a C-arm. The different recording positions 5 of the X-ray source 6 are achieved in that the C-arm is rotated such that the target volume 2 remains centrally in the acquisition region. This is combined with a compensation movement of the recording arrangement including the X-ray source 6 and the X-ray detector 7 along the central ray 8, so that the X-ray source 6 and thus the recording position 5 are situated on the recording trajectory 1. In this way, significantly more different recording geometries for the individual projection images are achieved.

Figure 5:
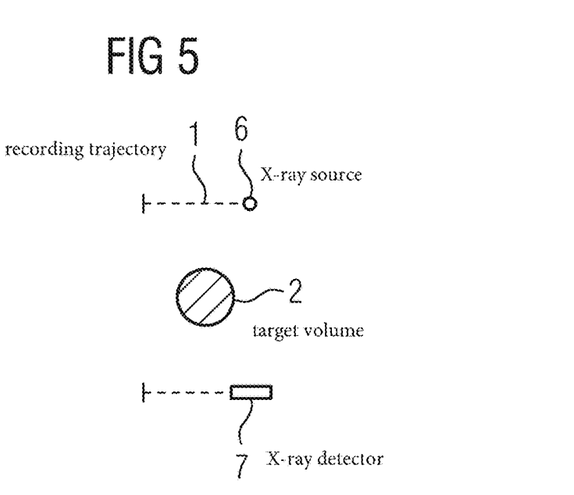
FIGS. 5 to 7 illustrate a third possibility for realizing a linear recording trajectory.
Figure 6:
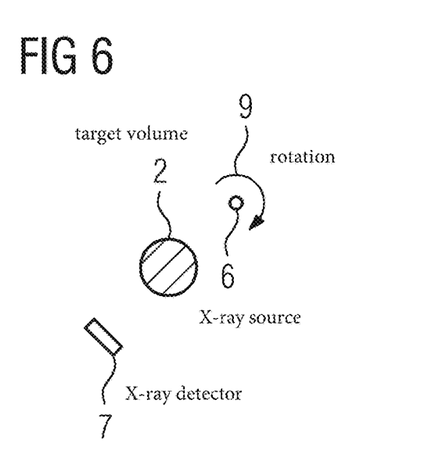
Figure 7:
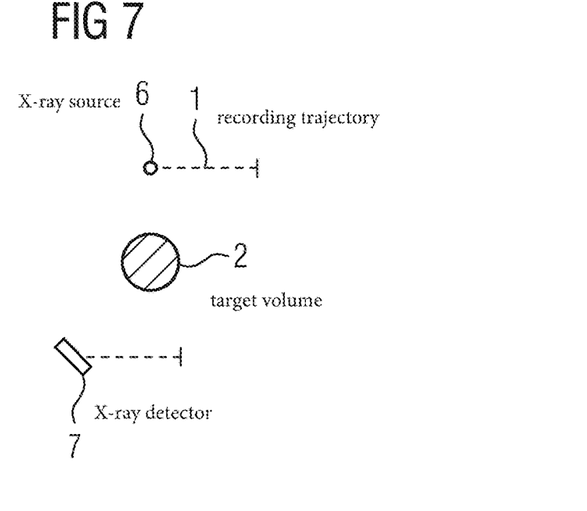

FIGS. 5 to 7 explain a further variant for implementing the linear recording trajectory 1. As shown in FIG. 5, the X-ray source 6 and the X-ray detector 7 are moved, ultimately comparably to FIG. 3, in parallel while recording a plurality of projection images. Thereafter, a rotation of the recording arrangement takes place, as indicated by the arrow 9, about the X-ray source 6, so that the target volume 2 again comes to lie in the acquisition region of the X-ray detector 7. There then occurs, as shown in FIG. 7, a parallel displacement of the X-ray source 6 and of the X-ray detector 7 while recording further projection images. For the displacement of the X-ray source 6, the linear recording trajectory 1 is used again. This may be repeated in further pivot positions about the X-ray source 6.

In all cases, two-dimensional projection images of different recording geometries are created, the reconstruction rules and deconvolution rules of which may be similarly formulated based on the linear recording trajectory 1, in each case, on two-dimensional reconstruction planes 4.

Accordingly, returning to FIG. 1, in acts S2 and S3, the reconstruction (e.g., two-dimensional reconstruction) and the deconvolution (e.g., two-dimensional deconvolution) then take place on the individual reconstruction planes 4. The deconvolution also, as is described in greater detail below, may be integrated into the reconstruction, so that acts S2 and S3 form a common reconstruction step.

Since artificial intelligence may be implemented with little effort and realiably, in the present case, a deconvolution algorithm of artificial intelligence that has been trained in act S4 is also used. As training data for training in act S4, for example, computed tomography data records with complete projection data acquisition and correspondingly associated projection images may thereby be used. Alternatively, simulation results and/or of scans with a phantom may be used. For simulation, for example, a computed tomography data record and/or another known object for which virtual projection images are calculated by simulation of the imaging (e.g., forward projection) in the recording geometries also used in the actual method may be used. Hereby, a noise term may also be included additively. It is therefore possible to generate a large quantity of training data in order to train the deconvolution algorithm (e.g., a Deep Natural Network (DNN)) in act S4.

Hereby, optionally, broad optimization conditions may also be integrated into the target function during training (e.g., an edge enhancement). The corresponding additional optimization is then integrated into the deconvolution kernel formed as the result of the training act S4.

In one embodiment, the deconvolution algorithm may thereby implement both the reconstruction in act S2 and also the deconvolution in act S3.

Thereby, for example, the recently made discoveries in the articles by C. Syben et al. mentioned in the general description part may be used, for example, in that the deconvolution and possibly further optimization conditions are finally integrated into the filter kernel of the filtered back projection that is to be determined.

The acts S2 and S3 may also be carried out separately, for example, as late as in a reconstruction step in which a two-dimensional reconstruction on the reconstruction planes 4 may take place (e.g., by filtered back projection). In act S3, in a deconvolution step, the deconvolution is carried out (e.g., by a deconvolution algorithm of artificial intelligence).

In an optional act S5, an adjustment algorithm is used in order to adjust the deconvolutions to one another on adjacent reconstruction planes 4 using a proximity relationship. For example, an optimization of the L1-norm of adjacent reconstruction planes 4 may take place.

In act S6, the reconstruction planes 4 lying, in the X-ray beam geometry, at an angle to one another and thus the reconstructed and deconvoluted sectional images lying at an angle to one another are converted into a typical, Cartesian voxel-defining three-dimensional image matrix (e.g., by the reformatting). The tomosynthesis data record improved in image quality at least with regard to blurring may then be output (e.g., for storing, for imaging, and/or for further processing).

Figure 8:
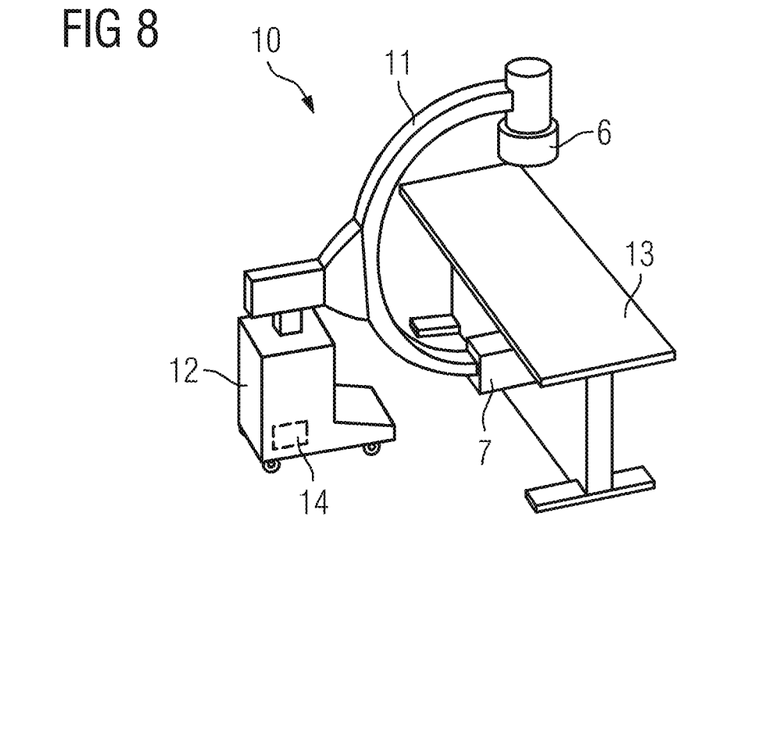
FIG. 8 illustrates one embodiment of an X-ray apparatus.

FIG. 8 shows an exemplary embodiment of an X-ray apparatus 10. The X-ray apparatus 10 has a C-arm 11 on which an X-ray generator 6 and an X-ray detector 7 are arranged mutually opposite as components of the recording arrangement. A variety of actuators permit a movement of the C-arm 11, which is supported by a base 12 in different translational and rotational degrees of freedom in order, as described, to be able to implement the linear recording trajectory 1. A part of this degree of freedom is implemented by the mobility of the base 12 (e.g., mobile C-arm). A patient may be positioned on a patient table 13. The operation of the X-ray apparatus 10 is controlled by a control device 14 (only indicated here), which is also configured for carrying out the method of one or more of the present embodiments.

Figure 9:
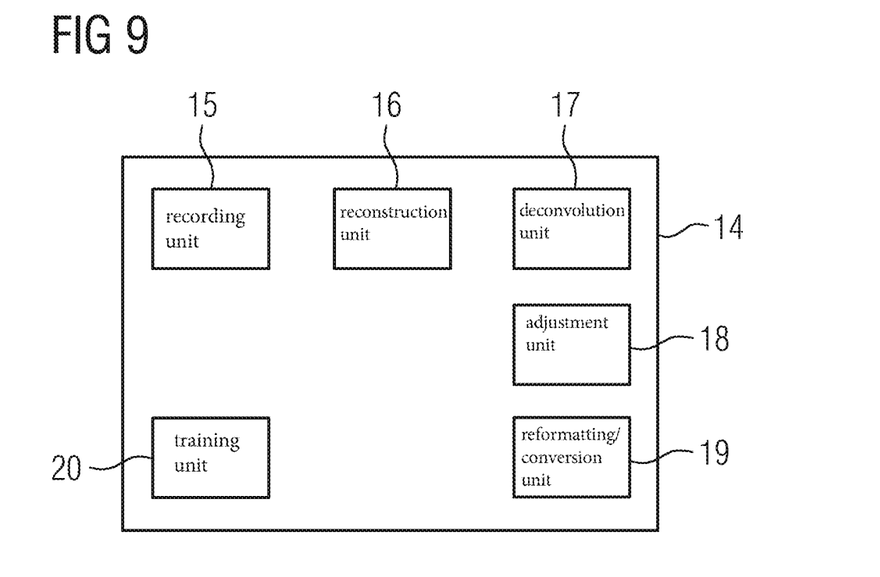
FIG. 9 illustrates the functional structure of one embodiment of a control device of the X-ray apparatus according to FIG. 8.

FIG. 9 shows the functional structure of the control device 14 in greater detail. The control device 14 has a recording unit 15 that controls the recording operation of the recording arrangement and the selection of corresponding recording geometries in order to record the projection images in act S1. A reconstruction unit 16 and a deconvolution unit 17 are provided for carrying out the corresponding acts S2 and S3, where the deconvolution unit 17 may also be integrated into the reconstruction unit 16 as described.

In an optional additional unit 18, the adjustment algorithm of act S5 may be carried out, while in a reformatting and/or conversion unit 19, the conversion from the reconstruction planes 4 into the image matrix may take place. The control device 14 also may also have a training unit 20 for carrying out the act S4, although this may also take place externally to the control device 14.

Although the invention has been illustrated and described in detail with the exemplary embodiments, the invention is not restricted by the examples disclosed. Other variations may be derived therefrom by a person skilled in the art without departing from the protective scope of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for establishing a three-dimensional (3D) tomosynthesis data record of a target volume from two-dimensional (2D) projection images recorded with a recording arrangement comprising an X-ray source and an X-ray detector in different recording geometries, the method comprising:
reducing image artifacts of the 3D tomosynthesis data record occurring due to lacking information using a deconvolution technique during or after a 2D reconstruction step,
wherein the 2D projection images are recorded along a linear recording trajectory of the X-ray source,
wherein the 2D reconstruction step and the use of the deconvolution technique take place in each 2D reconstruction plane of a plurality of different 2D reconstruction planes rotated relative to one another about the recording trajectory, wherein each 2D reconstruction plane is spanned by the linear recording trajectory and, in each case, a definition point in the target volume, and
wherein reconstruction is carried out independently on each of the 2D reconstruction planes defined by a different definition point.

2. The method of claim 1, wherein the recording arrangement is arranged on a C-arm.

3. The method of claim 2, wherein the recording trajectory is realized at least partially by a movement of the C-arm perpendicularly to a plane of extension of the C-arm.

4. The method of claim 2, wherein on a rotation of the C-arm, the recording arrangement is moved in a compensating manner along a central ray.

5. The method of claim 2, wherein on a rotation of the C-arm while maintaining alignment of the X-ray source to a central point of the target volume, the recording arrangement is moved in a compensating manner along a central ray.

6. The method of claim 1, wherein after a subsection of the movement of the X-ray source along the recording trajectory with a parallel movement of the X-ray detector, a rotation of the recording arrangement around the X-ray source takes place such that the target volume is situated in an acquisition region of the recording arrangement, and wherein the movement of the X-ray tube along the recording trajectory is continued with a parallel movement of the X-ray detector.

7. The method of claim 1, wherein a deconvolution algorithm of artificial intelligence that has been trained by machine learning and is to be used for the deconvolution, that describes a deconvolution kernel, or that determines an item of deconvolution information that describes a deconvolution kernel and is to be utilized for the deconvolution in all 2D reconstruction planes of the plurality of different 2D reconstruction planes is used.

8. The method of claim 7, wherein a result of a simulation, a scan, or the simulation and the scan is useable as training data for training the deconvolution algorithm.

9. The method of claim 8, wherein the result of the scan is useable as training data for training the deconvolution algorithm, and
wherein the scan is with a phantom.

10. The method of claim 8, wherein for the simulation, virtual projection images of a known object are calculated, at least one noise effect is added in the context of the simulation, or a combination thereof.

11. The method of claim 7, wherein, on training the deconvolution algorithm, at least one additional optimization condition is used for further improvement of image quality.

12. The method of claim 11, wherein the at least one additional optimization condition includes a low pass filtration, an edge enhancement, or a low pass filtration and an edge enhancement.

13. The method of claim 1, wherein the 2D reconstruction step takes place on the plurality of different 2D reconstruction planes according to filtered back projection.

14. The method of claim 1, wherein the deconvolution is carried out integrated into the reconstruction.

15. The method of claim 1, further comprising, after the deconvolution, an adjustment step making use of a proximity relationship between two adjacent reconstruction planes, of the plurality of different 2D reconstruction planes, rotated relative to one another.

16. An X-ray apparatus comprising:
a recording arrangement comprising:
an X-ray source;
an X-ray detector; and
a controller configured to establish a three-dimensional (3D) tomosynthesis data record of a target volume from two-dimensional (2D) projection images recorded with the recording arrangement in different recording geometries, the establishment of the 3D tomosynthesis data record comprising:
reduction of image artifacts of the 3D tomosynthesis data record occurring due to lacking information using a deconvolution technique during or after a 2D reconstruction step,
wherein the 2D projection images are recorded along a linear recording trajectory of the X-ray source,
wherein the 2D reconstruction step and the use of the deconvolution technique take place in each 2D reconstruction plane of a plurality of different 2D reconstruction planes rotated relative to one another about the recording trajectory, wherein each 2D reconstruction plane is spanned by the linear recording trajectory and, in each case, a definition point in the target volume, and
wherein reconstruction is carried out independently on each of the 2D reconstruction planes defined by a different definition point.

17. In a non-transitory computer-readable storage medium that stores instructions executable by one or more processors to establish a three-dimensional (3D) tomosynthesis data record of a target volume from two-dimensional (2D) projection images recorded with a recording arrangement comprising an X-ray source and an X-ray detector in different recording geometries, the instructions comprising:
reducing image artifacts of the 3D tomosynthesis data record occurring due to lacking information using a deconvolution technique during or after a 2D reconstruction step,
wherein the 2D projection images are recorded along a linear recording trajectory of the X-ray source,
wherein the 2D reconstruction step and the use of the deconvolution technique take place in each 2D reconstruction plane of a plurality of different 2D reconstruction planes rotated relative to one another about the recording trajectory, wherein each 2D reconstruction plane is spanned by the linear recording trajectory and, in each case, a definition point in the target volume, and
wherein reconstruction is carried out independently on each of the 2D reconstruction planes defined by a different definition point.

\* \* \* \* \*